US005958844A

United States Patent [19]

Sinquin et al.

[11] Patent Number: 5,958,844

[45] Date of Patent: Sep. 28, 1999

[54] METHOD OF TRANSPORTING HYDRATES SUSPENDED IN PRODUCTION EFFLUENTS

[75] Inventors: Anne Sinquin, Nanterre; Marie Velly, Montesson; Gérard Hillion, Herblay; Jean-Pierre Durand, Chatou, all of France

[73] Assignee: Institut Francais du Petrole, Rueil Malmaison Cedex, France

[21] Appl. No.: 09/160,289

[22] Filed: Sep. 25, 1998

[30] Foreign Application Priority Data

Jul. 25, 1997 [FR] France .................................. 97 12050

[51] Int. Cl.$^{6}$ ................................ C09K 3/00; C07C 9/00

[52] U.S. Cl. ................................ 507/90; 585/15; 585/950

[58] Field of Search ................................ 507/90; 585/15, 585/950

[56] References Cited

U.S. PATENT DOCUMENTS

| | | | |
|---|---|---|---|
| 4,973,775 | 11/1990 | Sugier et al. | 585/15 |
| 5,244,878 | 9/1993 | Sugier et al. | 507/90 |
| 5,491,269 | 2/1996 | Colle et al. | 585/15 |
| 5,841,010 | 11/1998 | Rabeony et al. | 585/15 |

FOREIGN PATENT DOCUMENTS

| | | |
|---|---|---|
| 0 323 775 | 7/1989 | European Pat. Off. . |

*Primary Examiner*—Philip Tucker

*Attorney, Agent, or Firm*—Millen, White, Zelano & Branigan, P.C.

[57] ABSTRACT

A method of transporting hydrates suspended in a fluid comprising water, a gas and a liquid hydrocarbon is described in which at least one non-ionic amphiphilic composition obtained by reacting at least one polymerized unsaturated vegetable oil with an aminoalcohol is incorporated into the fluid. The non-ionic amphiphilic composition is generally introduced in a concentration of 0.1% to 5% by weight with respect to the water.

27 Claims, No Drawings

METHOD OF TRANSPORTING HYDRATES SUSPENDED IN PRODUCTION EFFLUENTS

FIELD OF THE INVENTION

The invention relates to a method of transporting hydrates of natural gas, petroleum gas or other gases suspended in a fluid comprising water, one of those gases and a liquid hydrocarbon.

More particularly, it relates to a method which uses a non-ionic amphiphilic composition obtained by reacting at least one polymerised unsaturated vegetable oil with at least one aminoalcohol.

BACKGROUND OF THE INVENTION

Gases which form hydrates can in particular comprise at least one hydrocarbon selected from methane, ethane, ethylene, propane, propene, n-butane and isobutane, and possibly $H_2S$ and/or $CO_2$.

Such hydrates form when water is found in the presence of gas, either in a free state or dissolved in a liquid phase such as a liquid hydrocarbon, and when the temperature reached by the mixture, in particular water, gas and possibly liquid hydrocarbons such as oil, drops below the thermodynamic hydrate formation temperature, that temperature being given for a known composition of gases at a fixed pressure.

Hydrate formation is feared in particular in the gas and oilwell industry where the hydrate formation conditions can be satisfied. In order to reduce the production costs of crude oil and gas, both as regards investment and exploitation, one route, particularly for offshore production, is to reduce or even do away with drying treatments carried out on the crude or on the gas to be transported from the field to the coast and in particular to leave all or part of the water in the fluid to be transported. Offshore treatments are generally carried out on a platform located on the surface near the field, such that the effluent, which is initially hot, can be treated before the thermodynamic hydrate formation conditions are satisfied when seawater cools the effluent.

However in practice, when the thermodynamic conditions required for hydrate formation are satisfied, hydrate agglomeration causes the transport conduits to block through the formation of plugs which prevent the passage of any crude oil or gas.

Hydrate plug formation can cause a production stoppage and thus result in substantial financial losses. Further, restarting the installation, especially when it involves offshore production or transport, can be a long process, as it is difficult to decompose the hydrates which have formed. When the production from an undersea natural gas or crude oil and gas field comprising water reaches the surface of the sea bed and is then transported along the sea bottom, the reduction in the temperature of the effluent produced can mean that the thermodynamic conditions for hydrates to form are satisfied and they form, agglomerate and block the transfer conduits. The sea bottom temperature can, for example, be 3° C. or 4° C.

Favourable conditions for hydrate formation can also be satisfied onshore when conduits are not buried (or are not buried deeply) in the soil, for example when the ambient air temperature is low.

In order to overcome these disadvantages, prior authors have sought products which when added to a fluid can act as inhibitors by reducing the thermodynamic hydrate formation temperature. They are mainly alcohols, such as methanol, or glycols such as mono-, di- or tri-ethylene glycol. This solution is very expensive as the quantity of inhibitors which have to be added can be as high as 10% to 40% of the amount of water and the inhibitors are difficult to recover completely.

Insulation of the transport conduits has also been recommended, to prevent the temperature of the transported fluid from reaching the hydrate formation temperature under the operating conditions. However, this technique is also very expensive.

Further, a variety of non-ionic or anionic surfactant compounds have been tested for their retarding effect on hydrate formation in a fluid comprising a gas, in particular a hydrocarbon, and water. An example can be found in the article by Kuliev et al.: "Surfactants Studied as Hydrate Formation Inhibitors", Gazovoe Delo n° 10, 1972, 17–19, reported in Chemical Abstracts 80, 1974, 98122r.

The use of additives which can modify the hydrate formation mechanism have also been described where, instead of rapidly agglomerating together to form plugs, the hydrates formed disperse in the fluid without agglomerating and without obstructing the conduits. Examples in this regard are the Assignee's European patent application EP-A-0 323 774 which describes the use of non-ionic amphiphilic compounds selected from esters of polyols and carboxylic acids, which may or may not be substituted, and compounds containing an imide function; the Assignee's European patent application EP-A-0 323 775, which describes the use of compounds of the family of fatty acid diethanolamides or fatty acid derivatives; U.S. Pat. No. 4 856 593 which describes the use of surfactants such as organic phosphonates, phosphate esters, phosphonic acids, their salts and their esters, inorganic polyphosphates and their esters, and polyacrylamides and polyacrylates; and European patent application EP-A-0 457 375, which describes the use of anionic surfactants such as alkylarylsulphonic acids and their alkali metal salts.

Amphiphilic compounds obtained by reacting at least one succinic derivative selected from the group formed by polyalkenylsuccinic anhydrides and acids with at least one polyethylene glycol monoether have also been proposed for reducing the tendency of hydrates of natural gas, petroleum gas or other gases to agglomerate (EP-A-0 582 507).

SUMMARY OF THE INVENTION

We have now discovered that, to transport hydrates suspended in a fluid comprising water, a gas and a liquid hydrocarbon, it is particularly advantageous to use one or more non-ionic amphiphilic compositions obtained by reacting at least one polymerised unsaturated vegetable oil with at least one aminoalcohol as an additive.

Thus the invention provides a method of transporting hydrates suspended in a fluid comprising at least water, a gas and a liquid hydrocarbon under conditions in which hydrates can form from the water and the gas, characterized in that an additive comprising at least one non-ionic amphiphilic composition obtained by reacting at least one polymerised unsaturated vegetable oil with at least one aminoalcohol is incorporated into said fluid.

Such compositions and their preparation have been described in the French patent application filed on the same day by the Applicant, with the national registration number 97/12049. The contents of that application is hereby included in the present description by reference.

The viscosity of the polymerised unsaturated vegetable oils used to prepare the compositions used in the method of the present invention is usually viscosity in the range 5 to 60 Pa.s. These polymerised unsaturated vegetable oils have been widely described in the literature and are, for example, obtained by heat treating highly unsaturated oils such as linseed oil, or safflower oil, grapeseed oil, chinawood (Tung) oil or sunflower oil.

The aminoalcohols used to prepare the compositions used in the method of the present invention are, for example, selected from:

aminated monoalcohols such as
- monoethanolamine: $OH—(CH_2)_2—NH_2$;
- monopropanolamine: $OH—(CH_2)_3—NH_2$;
- monoisopropanolamine: $CH_3—CH(OH)—CH_2—NH_2$;
- 2-amino-1-butanol: $CH_3—CH_2—CH(NH_2)—CH_2\text{-}OH$;
- 1-amino-2-butanol: $CH_3—CH_2—CH(OH)—CH_2—NH_2$;
- N-methyl-ethanolamine: $CH_2—NH—(CH_2)_2—OH$;
- N-butyl ethanolamine: $CH_2—(CH_2)_3—NH—(CH_2)_2—OH$;
- pentanolamine, hexanolamine, cyclohexanolamine or polyalkanolamines;
- or polyalkoxyglycolamines with formula:

$$OH—(CH_2—CH_2O)_n—CH_2—CH_2—NH_2$$

where n represents the degree of polymerisation of the polyalkoxyglycol;

and aminated polyols such as:
- diethanolamine: $(OH—CH_2—CH_2)_2—NH$;
- diisopropanolamine: $(CH_2—CH(OH)—CH_2)_2—NH_2$, or
- trihydroxymethylaminomethane: $((HO)H_2C—)_3C—NH_2$.

The compositions used in the method of the present invention can be synthesised by reacting an excess of aminoalcohol, preferably diethanolamine, with a polymerised unsaturated vegetable oil preferably obtained from linseed oil.

The reaction is generally carried out in the absence of solvent at a temperature which is in the range 100° C. to 200° C., for example.

At the end of the reaction, a solvent is added to obtain a pumpable mixture. A certain number of solvents can be used, in particular aromatic cuts; however, any solvent derived from animal or vegetable oils or fats is preferred, to obtain a biodegradable solution of additives which does not pollute the environment. Advantageously, esters of $C_1$ to $C_4$ monoalcohols and $C_6$ to $C_{22}$ fatty acids derived from vegetable oils or fats are used, selected, for example, from coprah oil, babassu oil, palm-nut oil, tucum oil, murumuru, palm oil, shea oil, olive oil, peanut oil, kapok oil, bitter date oil, papaw oil, colocynth oil, croton oil, tiger nut oil, spurge oil, hemp oil, beechnut oil, gumbo oil, pulghere oil, camelina oil, safflower oil, niger oil, sunflower oil, oleic sunflower oil, rubber-seed oil, cocoa oil, purga, walnut oil, corn oil, soya oil, cottonseed oil, sorghum oil, grapeseed oil, linseed oil, tobacco oil, common pine-tar oil, afzelia oil, swede oil, mustard seed oil, brown mustard seed oil, wood oil, candlenut oil, tung oil, amoora oil, fir, crambe oil, perilla, erucic rapeseed oil, new rapeseed oil, oleic rapeseed oil, sesame seed oil, cocoa butter, tall oil, wheatgerm oil and castor oil; animal oils such as fish oils, as they are or partially hydrogenated; and animal fats such as lard, tallow and melted butter. Preferred esters are the methyl or ethyl esters.

The amount of solvent in the final mixture will be in the range 20% to 80% by weight, preferably in the range 30% to 70% by weight.

When used as additives to reduce the tendency of hydrates to agglomerate, these compositions are added to the fluid to be treated in concentrations which are Generally in the range 0.1% to 5% by weight, preferably 0.2% to 2% by weight with respect to the water.

In order to test the effectiveness of the products used in the method of the invention, the transport of hydrate-forming fluids such as oilwell effluents was simulated and hydrate formation tests were carried out using gas, the condensate and water in the apparatus described below.

The apparatus comprised a 10 meter loop constituted by 7.7 mm diameter tubes, a 2 liter reactor comprising an inlet and an outlet for gas, and an intake and a discharge for the mixture. The reactor enabled the loop to be pressurised. Tubes with an analogous diameter to those of the loop allowed the fluid to circulate from the loop to the reactor and vice versa, by means of a gear pump placed between the two. A sapphire cell integrated into the circuit enabled the circulating liquid as well as the hydrates to be observed when they formed.

In order to determine the effectiveness of the additives of the invention, the fluid (water, oil, additive) was introduced into the reactor. The apparatus was then pressurised to 7 MPa. The solution was homogenised by circulating it in the loop and reactor, then solely in the loop. By following the variations in the pressure drop and the flow rate, a rapid reduction in temperature from 17° C. to 4° C. (below the hydrate formation temperature) was imposed, then kept at that value.

The test period could be between a few minutes to several hours: a high performance additive could maintain circulation of the hydrate suspension with a stable pressure drop and flow rate.

The entire disclosure of all applications, patents and publications, cited above and below, and of corresponding French application 97/12050 filed on Sep. 25, 1997 are hereby incorporated by reference.

The following examples illustrate the invention but in no way should be considered to limit its scope. Example 4 is given by way of comparison.

EXAMPLE 1

52 kg of polymerised linseed oil with a viscosity of 10 Pa.s and 28 kg of diethanolamine were introduced into a 100 liter reactor. It was heated for 1 hour at 160° C. After cooling, the reaction product was diluted to 50% by weight in a hydrocarbon cut with an initial boiling point of 181° C. And an end point of 212° C.

EXAMPLE 2

Example 1 was repeated, with the exception that the reaction product was diluted to 50% by weight in a castor oil methyl ester.

EXAMPLE 3

Example 2 was repeated, the only difference being that the reaction product was diluted to 50% by weight in a rapeseed oil methyl ester.

EXAMPLE 4 (comparative)

In this example, a fluid composed of 10% by volume of water and 90% by weight of condensate was used.

The composition by weight of the condensate was:

for molecules containing less than 11 carbon atoms:

20% of paraffins and isoparaffins, 48% of naphthenes, 10% of aromatics; and for molecules containing at least 11 carbon atoms:

22% of a mixture of paraffins, isoparaffins, naphthenes and aromatics.

The gas used contained 98% by volume of methane and 2% by volume of ethane. The experiment was carried out at a pressure of 7 MPa, kept constant by adding gas. Under these conditions, a plug was observed to form in the coil several minutes after hydrates began to form (at a temperature of about 10.8° C.): the hydrates formed a blockage and fluid circulation became impossible.

EXAMPLE 5

This example repeated comparative Example 4 with the same fluid, the same gas and at the same pressure, but 1% by weight with respect to the water of the product produced in Example 1 was added to the circulating fluid. Under these conditions, an increase in the pressure drop was observed during hydrate formation (at a temperature of about 10° C.) followed by its reduction and stabilisation for a period of more than 24 hours at a temperature of 4° C. A reduction in temperature to 0° C. did not affect circulation of the suspension, and the hydrates remaining dispersed in the fluids.

EXAMPLE 6

Example 5 was repeated, with the exception that 1% by weight with respect to the water of the product prepared in Example 2 was used. Under these conditions, fluid circulation was observed to be maintained for more than 4 hours at 4° C.

EXAMPLE 7

Example 5 was repeated, with the exception that 1% by weight with respect to the water of the product prepared in Example 3 was used. Under these conditions, fluid circulation was observed to be maintained for more than 24 hours at 4° C. A reduction in temperature to 0° C. did not affect circulation of the suspension, the hydrates remaining dispersed in the fluids.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method comprising transporting hydrates suspended in a fluid comprising at least water, a gas and a liquid hydrocarbon under conditions in which hydrates can form from the water and the gas, characterized in that an additive comprising at least one non-ionic amphiphilic composition obtained by reacting at least one polymerised unsaturated vegetable oil with at least one aminoalcohol is incorporated into said fluid, said polymerised unsaturated vegetable oil comprising glycerides of unsubstituted, unsaturated hydrocarbyl carboxylic acids prior to polymerization.

2. A method according to claim 1, characterized in that said polymerised unsaturated vegetable oil is a polymerised linseed oil.

3. A method according to claim 2 wherein the viscosity of said polymerised linseed oil is in the range 5 to 60 Pa.s. at 20° C.

4. A method according to of claim 1, wherein the aminoalcohol is diethanolamine.

5. A method according to of claim 1, wherein the additive is contained in a solvent consisting of an aromatic cut.

6. A method according to claim 1, wherein the additive is contained in a solvent derived from an animal or vegetable oil or fat.

7. A method according to claim 6, wherein, characterized in that the solvent for the additive is a methyl ester of rapeseed oil.

8. A method according to claim 5, characterized in that the solvent is added so that the final mixture contains in the range 20% to 80% by weight, of solvent.

9. A method according to claim 1, wherein said non-ionic amphiphilic composition is incorporated into said fluid in a concentration of 0.1% to 5% by weight with respect to the water present.

10. A method according to claim 9, wherein said concentration is 0.2% to 2% by weight with respect to the water present.

11. A method according to claim 1, wherein in said fluid, said gas comprises at least one hydrocarbon selected from the group consisting of methane, ethane, ethylene, propane, propene, n-butane and isobutane, and optionally at least one of $H_2S$ and/or $CO_2$.

12. A method according to claim 1, wherein said fluid comprises natural gas.

13. A method according to claim 1, wherein, characterized in that said fluid comprises petroleum gas and at least one liquid hydrocarbon.

14. A method according to claim 6, wherein the solvent is added so that the final mixture contains in the range 20% to 80% by weight of solvent.

15. A method according to claim 7, wherein the solvent is added so that the final mixture contains in the range 20% to 80% by weight of solvent.

16. A method according to claim 8, wherein the range is 30 to 70% by weight.

17. A method according to claim 14, wherein the range is 30 to 70% by weight.

18. A method according to claim 15, wherein the range is 30 to 70% by weight.

19. A method according to claim 3, wherein the aminoalcohol is diethanolamine.

20. A method according to claim 9, wherein said concentration is 0.2% to 2% by weight with respect to the water present.

21. A method according to claim 1, wherein said polymerized unsaturated vegetable oil is a polymerized safflower oil.

22. A method according to claim 1, wherein said polymerized unsaturated vegetable oil is a polymerized grapeseed oil.

23. A method according to claim 1, wherein said polymerized unsaturated vegetable oil is a polymerized Chinawood oil.

24. A method according to claim 1, wherein said polymerized unsaturated vegetable oil is a polymerized sunflower oil.

25. A method comprising transporting hydrates suspended in a fluid comprising at least water, a gas and a liquid hydrocarbon under conditions in which hydrates can form from the water and the gas, characterized in that an additive comprising at least one non-ionic amphiphilic composition obtained by reacting at least one polymerised unsaturated vegetable oil with at least one aminoalcohol is incorporated into said fluid said, polymerized unsaturated vegetable oil comprising polyunsaturated hydrocarbyl carboxylic acids prior to polymerization.

26. A method according to claim 1, wherein said unsaturated vegetable oil is polymerized by heating.

27. A method according to claim 1, wherein said polymerized unsaturated vegetable oil comprises unsubstituted, polyunsaturated hydrocarbyl carboxylic acids prior to polymerization.

* * * * *